(12) United States Patent
Van Ausdall et al.

(10) Patent No.: US 6,625,558 B1
(45) Date of Patent: Sep. 23, 2003

(54) METHOD AND APPARATUS FOR TESTING CMOS IMAGE SENSORS

(75) Inventors: Terrence Lee Van Ausdall, Boulder Creek, CA (US); Rudolf A. Weidemann, Fremont, CA (US)

(73) Assignee: Zoran Corporation, Santa Clara, CA (US)

(*) Notice: Subject to any disclaimer, the term of this patent is extended or adjusted under 35 U.S.C. 154(b) by 0 days.

(21) Appl. No.: 09/434,097

(22) Filed: Nov. 5, 1999

(51) Int. Cl.⁷ .............................................. B07C 5/344
(52) U.S. Cl. .................... 702/117; 209/573; 250/559.19
(58) Field of Search ........................ 209/573; 710/101; 355/1; 359/172; 356/601; 435/6; 353/20; 362/554, 551, 558; 294/64.1; 29/762; 56/3.03–3.08, 614, 623, 625, 630, 631; 250/559.19, 559.22–559.31, 559.38, 216, 239, 559.2

(56) References Cited

U.S. PATENT DOCUMENTS

| | | | |
|---|---|---|---|
| 5,075,716 A | * 12/1991 | Jehan et al. ................... | 355/1 |
| 5,298,428 A | * 3/1994 | O'Rourke et al. .......... | 436/171 |
| 5,625,451 A | * 4/1997 | Schiff et al. ................ | 356/236 |
| 5,883,830 A | * 3/1999 | Hirt et al. ............... | 365/185.03 |
| 6,066,822 A | * 5/2000 | Nemoto et al. ............. | 209/573 |
| 6,122,084 A | * 9/2000 | Britz et al. ................. | 359/172 |
| 6,290,382 B1 | * 9/2001 | Bourn ......................... | 362/554 |
| 6,324,606 B1 | * 11/2001 | Lenehan et al. ............ | 710/101 |
| 6,326,142 B1 | * 12/2001 | Royer ............................. | 435/6 |

* cited by examiner

Primary Examiner—Marc S. Hoff
Assistant Examiner—Carol S Tsai
(74) Attorney, Agent, or Firm—Dag Johansen; Stattler Johansen & Adeli LLP (57) ABSTRACT

A method and apparatus which enables fast testing of light sensing integrated circuits is disclosed. The integrated circuit is positioned in a test head which includes a light source output providing a flat field light to shine on the light sensing portion of the integrated circuit under test. The light is provided to the light source output through an optical fiber from a light box which includes electronic filtering and shutter operations. Light is provided to the light box through another optical fiber from a precision light source. The operation of the light box, including adjusting filtering characteristics and shutter timing is controlled from a tester which also controls the integrated circuit under test in the test head. A high speed data link couples output signals from the test head to dedicated signal processing circuitry which analyzes the output signals to determine whether the integrated circuit passes or fails testing. The optical system including, for example, a liquid crystal filter which can be controlled very quickly, and the dedicated signal processor and high speed data link allows testing of integrated circuits to be carried out at a very high speed.

19 Claims, 5 Drawing Sheets

METHOD AND APPARATUS FOR TESTING CMOS IMAGE SENSORS

FIELD OF THE INVENTION

The present invention relates to the field of testing integrated circuits following fabrication. In particular, the present invention relates to a method and apparatus for testing image sensor circuits which is particularly well suited to the demands required of CMOS image sensor testers.

BACKGROUND OF THE INVENTION

Semiconductor image sensing devices are finding widespread application with the increased use of digital still cameras and digital video cameras. Charge coupled device (CCD) technology has hitherto dominated the market for such imagers. A more recent emerging technology involves forming image sensors using complementary metaloxide silicon (CMOS) processing. CMOS image sensors are advantageous in that the CMOS process allows for the inclusion of circuits for image processing and the like, allowing a high level of product.integration to enable virtually all electronic camera functions to be integrated on a single chip. Image sensors manufactured in CMOS can also be made relatively inexpensively and facilitate significant power savings compared to CCD sensors, which are particularly important characteristics for portable consumer applications.

However, the additional functionality which can be integrated into a CMOS image sensor chip also increases the testing requirements of the product following fabrication. The testing of image sensors is more difficult than most integrated circuits because of the optical input required and because of the mixed analog and digital nature of the circuitry. These factors, together with the additional image processing functions and the like which can be included, make assessing CMOS image sensors the most demanding task for any mixed signal tester. In order to maintain the inexpensive price of CMOS image sensors, the testing procedures and apparatus must therefore be able to efficiently and accurately complete assessment of the functions of the fabricated circuits and chips at high speeds and in large volumes.

SUMMARY OF THE INVENTION

In accordance with the principles of the present invention, there is provided a testing apparatus and method for testing image sensing integrated circuits. The testing apparatus includes a test head adapted to receive an integrated circuit under test, and the test head has electrical contacts for making electrical connections to the integrated circuit, and a light source output arranged to shine test light on a light sensing portion of the integrated circuit whilst it is connected to the electrical contacts. The testing apparatus also includes controlling circuitry coupled to communicate with the integrated circuit by way of the electrical connections to control functions of the integrated circuit during testing. The testing apparatus further includes dedicated processing circuitry coupled through a fast data channel to the integrated circuit by way of the electrical connections to receive output signals from the integrated circuit during testing. The dedicated processing circuitry is adapted to analyze the output signals for the purpose of determining whether the integrated circuit under test meets predetermined test criteria.

In the preferred form of the invention, the controlling circuitry is coupled to communicate with the dedicated processing circuitry, wherein the controlling circuitry communicates testing parameters and pass/fail test limits to the processing circuitry and the processing circuitry communicates to the controlling circuitry indications of whether the integrated circuit under test passes or fails testing according to the output signal analysis. Preferably the test head includes mechanical apparatus for inserting and positioning the integrated circuit under test to make connection to said electrical contacts and for removing the integrated circuit following completion of testing. The removing operation of the mechanical apparatus can be controlled by the controlling circuitry according to the indications of whether the integrated circuit under test passes or fails testing.

In the preferred form of the invention, the fast data channel coupling the integrated circuit under test to the dedicated processing circuitry comprises a low-voltage differential signal (LVDS) transfer connection. The dedicated processing circuitry may comprise a computer equipped with one or more digital signal processor cards which are dedicated to the task of processing and analyzing the output signals from the integrated circuit under test.

In a preferred form of the invention, the testing apparatus includes a white light source and a light box, wherein the light source is coupled to transmit light through a first optic fiber to the light box, and the light box is coupled to transmit light through a second optic fiber to the light source output in the test head. The light box preferably incorporates an electronic filter disposed in the path of light passing from the first optic fiber to the second optic fiber to allow light from the white light source to be modified in a controlled fashion before reaching the light source output. The light box may also incorporate an electronically controlled shutter. The electronic filter may include a neutral density tunable liquid crystal attenuator and/or an electronic color sequence filter. Preferably the electronic filter and shutter are controlled by the tester. Preferably the light source output comprises an integrating sphere device for providing a flat field light output and a tapered coherent fused fiber optic bundle to direct the flat field light to shine on the light sensing portion of the integrated circuit.

According to one form of the invention, the test head includes a base portion having a seat for positioning the integrated circuit under test, with the light source output being mounted to the base portion and an aperture being provided to allow light from the light source output to shine on the integrated circuit light sensing portion when positioned in the seat. The base portion may further have electrical contact elements for coupling signals to the controlling circuitry and the dedicated processing circuitry. In this form of the invention the test head may also include a connecting portion which is moveable between open and closed positions relative to the base portion, the connecting portion having electrical input contacts which provide connections between the electrical contact elements of the base portion and contacts of the integrated circuit under test when positioned in the seat and with the connecting portion in its closed position.

The present invention also provides a method for testing image sensing integrated circuits. The method includes providing a test head having a seat for positioning an integrated circuit under test in relation to a light source output and for making electrical connections to said integrated circuit. The method also includes providing light from a light source through a first optic fiber to a light box having electronic filter and shutter control and from the light box through a second optic fiber to the light source output to shine on a light sensing portion of the integrated circuit when positioned in the seat of the test head. First control signals are provided from a tester to the integrated circuit by way of the test head to control the integrated circuit during testing, and second control signals are provided to the light box to control the electronic filter and shutter during testing. The method includes transferring output signals from the integrated circuit during testing to processing circuitry by way of a high speed data channel coupled between the test head and the processing circuitry, and analyzing the output signals in the processing circuitry to determine whether the integrated circuit passes or fails testing.

Preferably the controlling circuitry communicates testing parameters and pass/fail test limits to the processing circuitry and the processing circuitry communicates to the controlling circuitry indications of whether the integrated circuit under test passes or fails testing according to the output signal analysis. Preferably also, the high speed data channel by which output signals are transferred to dedicated processing circuitry comprises a low-voltage differential signal (LVDS) connection.

Preferably the test head includes mechanical apparatus for inserting and positioning the integrated circuit under test to make connection to said electrical contacts and for removing the integrated circuit following completion of testing, the method further including controlling the removing operation of the mechanical apparatus by the controlling circuitry according to the indications of whether the integrated circuit under test passes or fails testing.

BRIEF DESCRIPTION OF THE DRAWINGS

The invention is described in greater detail hereinafter, by way of example only, through description of a preferred embodiment thereof and with reference to the accompanying drawings in which.

DETAILED DESCRIPTION OF THE PREFERRED EMBODIMENT

A method and apparatus for testing image sensor circuits is disclosed herein. In the following description, for purposes of explanation, specific nomenclature and specific implementation details are set forth to provide a thorough understanding of the present invention. However, it will be apparent to one skilled in the art that these specific details are not required in order to practice the present invention. For example, the preferred embodiment is described in the context of the testing apparatus for CMOS technology image sensors, but the apparatus is equally applicable to other types of image sensor circuits, for example CCD sensors. Also, several specific items of equipment from certain suppliers are indicated as being suitable for use in implementing the present invention, but those of ordinary skill in the art will recognize that other items of equivalent or similar function from the same or other suppliers could alternatively be employed.

Overview of an Image Sensor Testing Apparatus

The testing of image sensor integrated circuits is a relatively difficult and computationally challenging process. One of the reasons for the difficulties associated with testing image sensor circuits is that both optical and electrical inputs are required for testing, and outputs can be of mixed signal types involving both digital and analog signals and often involve large amounts of data. Testing of an integrated circuit is utilized to verify that the fabricated chip functions as it is designed to do, or at least performs to within certain predetermined tolerances with respect to the design specifications. In image sensing circuits, the testing includes verification of operation of each of the pixel circuits, as well as verification of additional processing circuitry and general electrical tests. Therefore, for mega-pixel class image sensors having of the order of $1.0 \times 10^6$ pixels (or more) in an array, a large number of tests must be completed for a single chip. Furthermore the pixel array tests require a significant amount of data to be conveyed from the device under test to the test processing apparatus.

Figure 1:
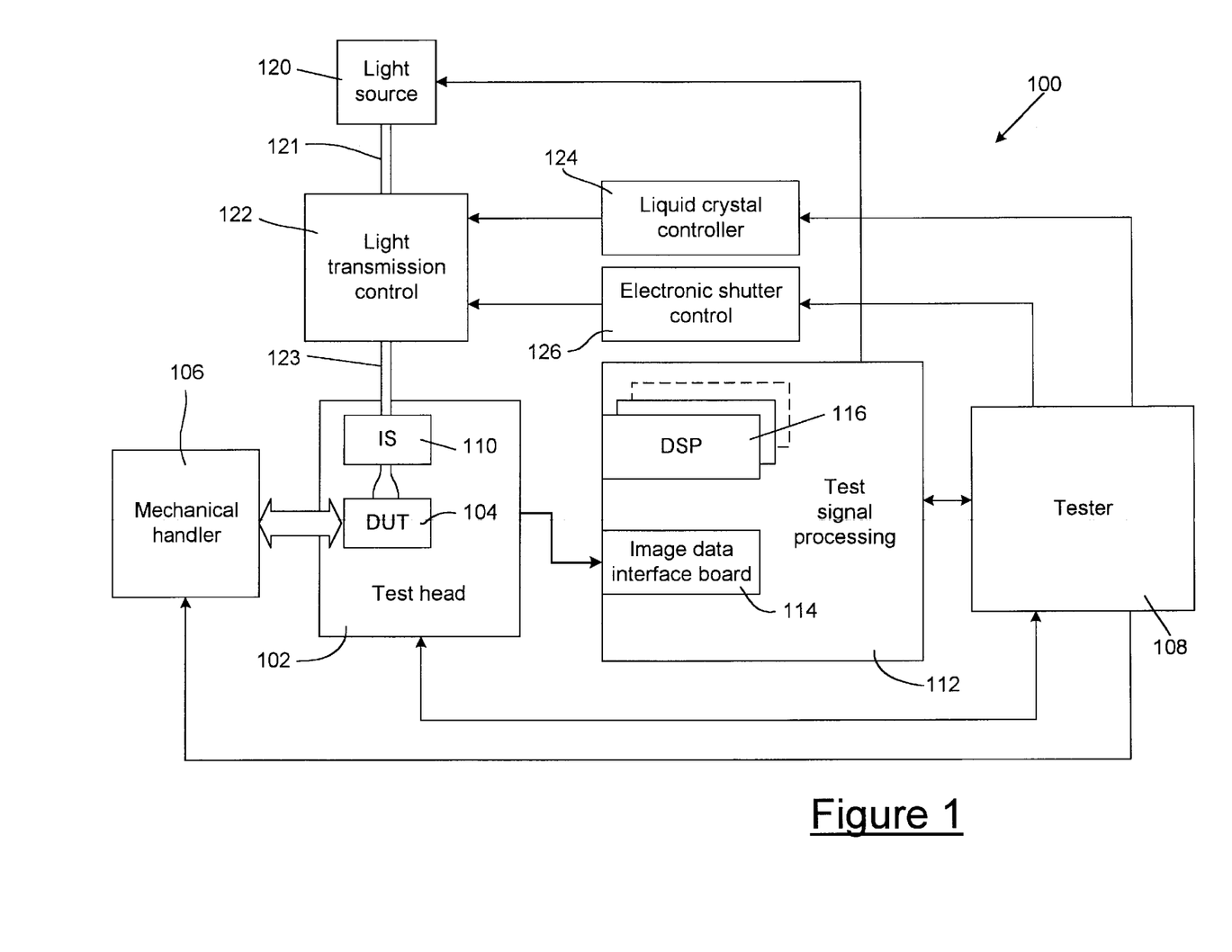
FIG. 1 is a block diagram of a testing apparatus in accordance with the present invention.

A preferred embodiment of an integrated circuit testing apparatus and method is described in detail hereinafter with particular reference to the accompanying drawings. Referring firstly to FIG. 1, a block diagram of an integrated circuit testing apparatus according to a preferred embodiment of the present invention is shown, indicated generally by the reference numeral 100. The testing apparatus 100 is constructed particularly for the purpose of testing mega-pixel class CMOS image sensors.

The testing apparatus 100 includes a test-head 102 which holds the device under test (DUT) 104. The device under test 104 in this case is an image sensing integrated circuit. A suitable test-head 102 is manufactured by Teradyne, Inc. of Boston, Mass., for use in mixed signal testing systems under the model number A585. A Teradyne model Integra J750 test system is also thought to be suitable, and other test heads from different manufacturers will be recognized by those skilled in the art as applicable alternatives. The test-head can be constructed for testing of integrated circuits whilst still part of the silicon wafer, or for testing the chips after the inclusion of lead connections and encapsulation. The following description relates to a test-head construction adapted for use with discrete, encapsulated image sensor chips, but it will be readily apparent to those skilled in the art that the teaching of the present invention can be also applied to testing apparatus' using a wafer test-head.

The test-head 102 has provision for seating of the DUT 104 and for making electrical connections to the contact leads thereof In the preferred embodiment of the present invention, the Teradyne A585 test-head has specific adaptations made thereto, which are described in greater detail hereinbelow with particular reference to FIGS. 2, 3 and 4.

The test-head 102 is coupled to a tester 108, which is also from the Teradyne A585 mixed signal tester product range. The tester 108 provides electrical control signals to the test-head 102. The control signals provided to the test-head from the tester 108 are effective to control operations of the test-head (the nature of which are described in greater detail below), as well as signals which are passed to the DUT in order to control the image sensor circuit during testing. The tester 108 also controls a mechanical handler 106 which operates in conjunction with the test-head to physically manipulate the DUT. In particular, the mechanical handler operates to place the DUT in position in the test-head before the test begins, and remove the DUT from the test-head following completion of the test. Preferably the mechanical handler is controlled by the tester 108 so as to separate those DUT's removed from the test-head according to the results of the testing, for example placing those devices which fail the testing separately from those which pass. A suitable form of mechanical handler is manufactured by Seiko-Epsom under the model name Hummingbird 3500.

The test-head 102 is also coupled to a test signal processor 112, the function of which is to process signals output from the DUT during testing. The test signal processor 112, in the preferred embodiment, is a Pentium III™ based computer operating under a Windows NT™ operating system. The signals output from the DUT during testing are passed from the test-head to the test signal processor 112 by way of a low-voltage differential signal (LVDS) transmission system. The LVDS transmission lines are coupled to an interface board 114 in the test signal processor 112, which is adapted to receive mixed signals at high data rates. Signals output from the DUT are buffered and fed to DS90LV031A LVDS drivers which drive the LVDS signals over a SCSI2 standard cable connection to the interface board. The LVDS interface may be of the type standardized as differential small-amplitude interfaces by P1596.3 which is one of the standardization committees of IEEE. This standard is explained in detail, for example, in a document referred to as "IEEE Draft Standard for Low-voltage Scalable Coherent Interface (SCI) Draft 1.20 (Jul. 13, 1995)". The interface board 114 may comprise, for example, a video capture board such as a PIXCI® D image transfer board, manufactured by EPIX, Inc. of Lexington Drive, Buffalo Grove, Ill. Such an image transfer board receives input signals through the LVDS interface, and couples to the PCI bus of the test signal processor computer 112.

The test output data is communicated within the test signal processor 112 from the interface board 114 to one or more digital signal processor (DSP) boards 116 by way of a high speed internal bus. The, or each, DSP board may comprise, for example, a Daytona single or dual TMS320C6701 PCI-based product available from Spectrum Signal Processing Inc. Each of such DSP boards can provide up to 2×1 gigaflops of processing power.

The test signal processor 112 is coupled to communicate with the tester 108 by way of a 10BaseT Ethernet network connection which enables data to be passed between the processor 112 and tester 108 as described in greater detail below.

As will be appreciated from the earlier introduction to image sensor testing requirements, for testing of the light sensing qualities of the circuitry a light source for the DUT is necessary. The light incident on the DUT during testing must be carefully controlled in order to obtain accurate testing results. In the testing apparatus 100, the preferred embodiment of the present invention provides controlled light to the DUT through an optical system comprising components 120, 121, 122, 123 and 110 shown in FIG. 1.

A light source 120 provides the illumination for the optical system. A suitable light source 120 is a DC regulated, light feedback fiber optic lightsource Model 3900 available from Illumination Technologies, Inc. of Syracuse, N.Y. The light source 120 is coupled by way of an RS-232 connection to the tests signal processor 112, which controls the output of the light source. In order to obtain consistent test results over a period of time, the light source is merely turned on to a desired light output before a testing batch and then turned off after testing has been completed. During operation the Illumination Technologies lightsource has very stable light output, accurate to 0.1%.

The light source 120 has a coupling for output to an optical fiber, which in this case is coupled to a 1000 um fiber optic cable 121. The fiber optic cable 121 conveys light from the light source 120 to a light transmission controller 122.

The light transmission controller 122 provides a number of functions, and is described in greater detail below in connection with FIG. 5. Light is output from the transmission controller 122 into another fiber optic cable 123, which is coupled at its output end to an integrating sphere (IS) component 110. The IS 110 is incorporated into the test-head 102 in fixed relationship to the position of the DUT during testing. The function of the IS 110 is to provide a spatially uniform light output from the fiber optic cable 123 to shine on the light sensing pixel array of the DUT 104.

Figure 5:
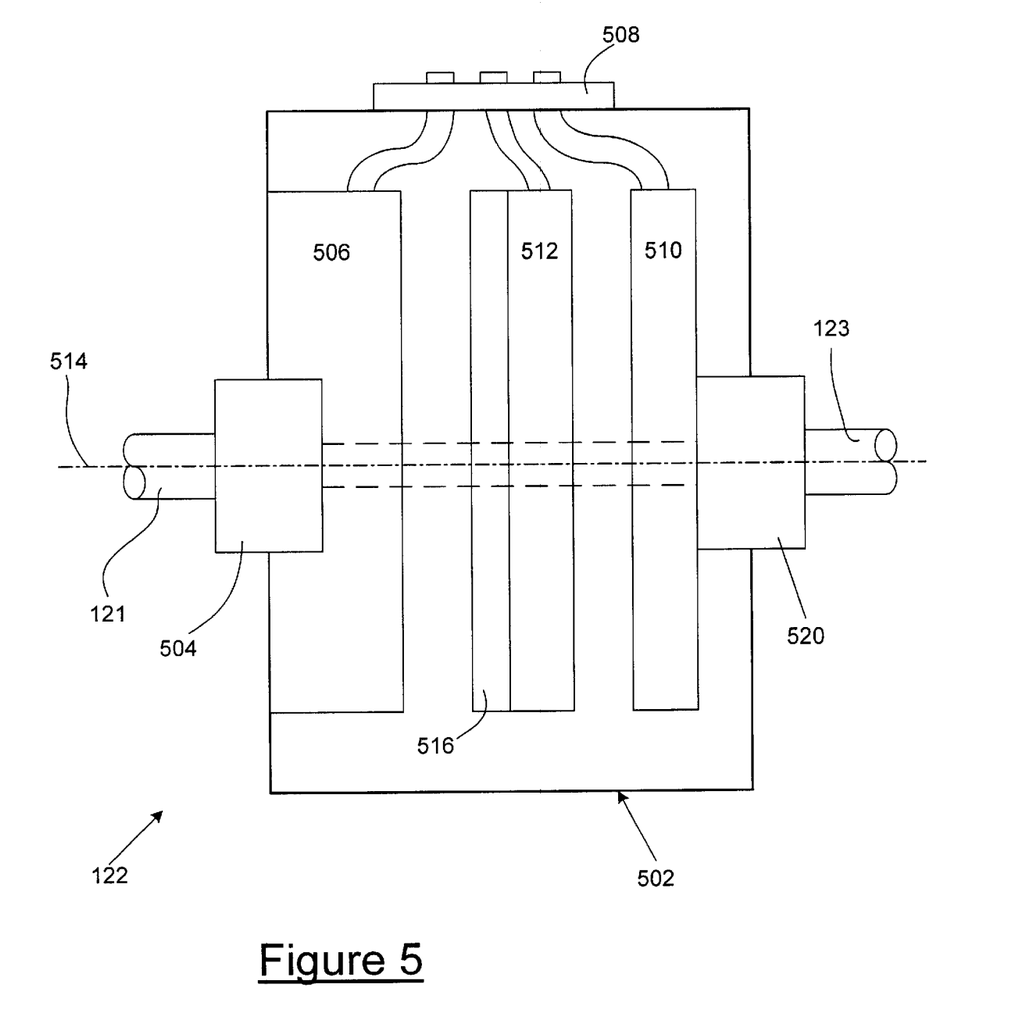
FIG. 5 is a cut-away view of a light transmission control component of the preferred embodiment.

Referring to FIG. 5, a cut-away view of a light transmission controller 122 is shown in simplified block diagram form. Input light is provided from the input fiber optic cable 121 and is passed through a shutter, an attenuating filter, a fixed color shift filter and optionally a controllable color sequence filter before entering the output optic fiber cable 123. The shutter, attenuating filter (and color sequence filter) are electronically controlled.

A casing 502 provides a structure so that the optical components of the transmission controller 122 can be mounted thereto and maintained in alignment. At one side of the casing 502 is an input optical fiber cable mounting 504 which in use receives an end of the fiber optic cable 121. The input optical fiber cable mounting 504 is provided with collimating lenses (not shown). Light output from the collimating lenses is passed through an electronically controlled shutter, for example of the type manufactured under the name of UNIBLITZ™ by Vincent Associates of Rochester, N.Y. The electronic shutter 506 is externally controlled from the tester 108 by way of an electronic shutter control 126 (see FIG. 1). The electronic shutter control 126 can be a UNIBLITZ™ D122 or T132 model shutter driver/timer, for example, also available from Vincent Associates. The electronic shutter control 126 is coupled to the shutter mechanism 506 by a suitable electrical connector through the electrical control interface panel 508, also mounted to the casing 502. The electronic shutter and shutter controller are capable of selective control of exposure and delay interval ranging from 0.1 ms upwardly.

On the casing 502 opposite the input fiber optic cable mounting, an output fiber optic cable mounting 520 is provided for coupling to the fiber optic cable 123. An attenuation filter 510 is mounted within the casing 502 in the optical path between the input and output optical fibers 121, 123. The attenuation filter 510 is similarly controlled from the tester 108, by way of a controller circuit 124 (FIG. 1). A suitable attenuation filter is manufactured by Cambridge Research & Instrumentation, Inc. (Boston, Mass.) under the VND-ANL series VariND Neutral Density Filter. Such an attenuation filter has a tunable liquid crystal attenuator element which is precisely controllable in its transmission characteristics with a response time of 50 milliseconds. In the transmission controller 122, the attenuation filter 510 is coupled to the electronic control circuit 124 by way of a suitable electrical connector through the electrical control interface panel 508.

A fixed color shift filter 516 is also mounted in the casing 502 in the optical path of light passing from input optical fiber 121 to output optical fiber 123. The glass fixed color shift filter 516 is provided to adjust the color temperature of light to shine on the DUT. This is desirable because the color temperature of the light from light source 120 may not be the color temperature required for the testing procedures. For example, it may be desirable to shift the color temperature of light from a relatively low color temperature provided from the light source to a higher color tempurature suitable for testing the DUT. Furthermore, the fixed color shift filter can be selected to adjust the light color to account for any color losses which may occur in the optical fibers 121 and 123.

The light transmission controller 122 may also include a color filter 512 for adjusting the color characteristics of light passing therethrough for various tests which may be desirable to be performed on the DUT. For example, a CRI VS-RGB-GP color sequence filter may be mounted within the casing 502 between the shutter 506 and attenuator 510, in the optical path along the optical axis 514 of the transmission controller. Such a color filter may be similarly controllable from the tester 108 by suitable electronic control circuitry (not shown).

The fiber optic cable 123 conveys the light from the transmission controller 122 to the integrating sphere mounted on the test-head 102. In order to shine light from the integrating sphere on the DUT, the test-head 102 is specially constructed as shown in FIGS. 2, 3 and 4. FIG. 2 is a conceptual view of the structure of the test-head mounting arrangement 200 of the preferred embodiment, shown in exploded cross-sectional profile. The mounting arrangement 200 allows electrical connections to be conveniently made to the DUT whilst permitting light from the IS to be incident on the pixel array of the light sensing circuit. The DUT is illustrated at 220 in FIG. 2, having electrical contacts 222 at one side thereof and a light transmission aperture at the other side 221 which allows light, in use, to reach the light sensing array of the DUT integrated circuit. The difficulty faced in constructing a mounting arrangement for the DUT is to allow electrical connections to be made to the DUT contacts and light to shine on the light sensing array, whilst allowing convenient insertion and removal of the DUT from the test-head for fast automated testing of large numbers of image sensors.

Figure 2:
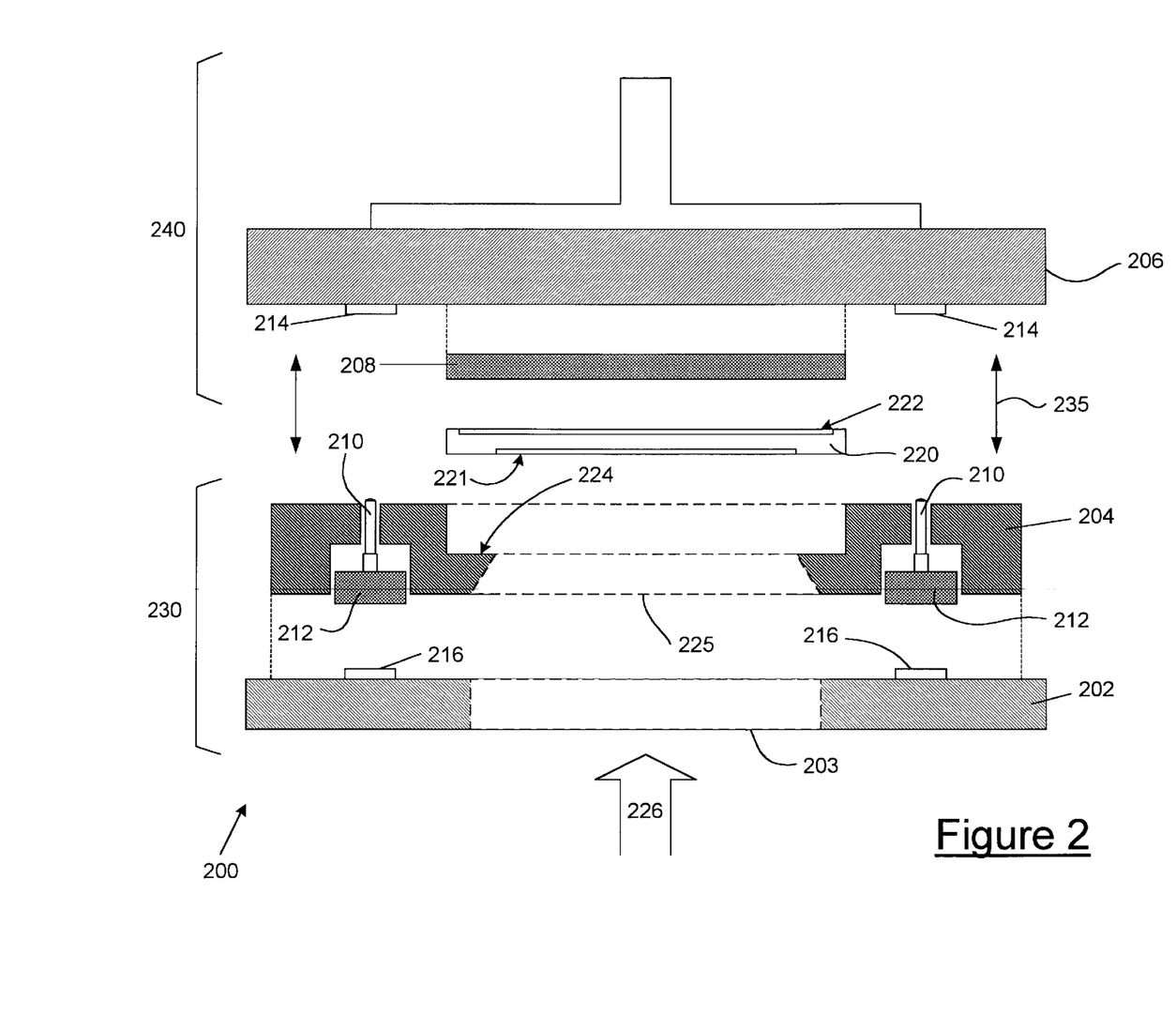
FIG. 2 is a conceptual drawing of a mounting arrangement for a device under test.

The mounting arrangement 200 shown in FIG. 2 has two main portions: a lower part 230 and an upper part 240. The lower part 230 of the mounting arrangement is based on an interface board 202, which is a relatively large circuit board mounted in and forming part of the test-head 102 (FIG. 1). The interface board has interconnections for communicating signals between the DUT and the tester 108 and signal processor 112 (FIG. 1). The interface board may have additional circuitry situated thereon performing interface/communication functions or the like. The interface board 202 has first contact lands 216 on an upper surface thereof surrounding a light transmission aperture 203. The contact lands 216 are electrically connected to the interconnecting tracks of the interface board.

A guide plate 204 is affixed to the interface board. The guide plate 204 has a light transmission aperture 225 aligned with the aperture 203 in the interface board. The guide plate is also formed with a seat 224 which is shaped to receive the DUT 220. When the DUT is positioned in the seat of the guide plate, the light sensing array side 221 is exposed to light which may shine in the direction of arrow 226 through the apertures 203 and 225 formed in the interface board and guide plate respectively. The guide plate has a peripheral structure which accommodates a plurality of contact elements 210. The contact elements 210 are in the form of pins which extend through respective holes in the guide plate peripheral structure. With the guide plate mounted to the interface board, lower ends of the contact elements are electrically coupled to the interface board contact lands through a first surface mount matrix 212. The other ends of the contact elements 210 extend from upper surface of the guide plate peripheral structure, away from the interface board.

The upper part 240 of the mounting arrangement 200 is moveable in relation to the lower part 230, toward and away from the upper surface of the guide plate as indicated by the arrows 235. Relative movement of the upper and lower parts of the mounting arrangement is effected by a mechanical handler 106 (FIG. 1) which is controlled by the tester 108. When the upper and lower parts of the mounting arrangement are positioned away from one another access is provided to the seat 224 of the guide plate, which enables DUT 220 to be placed in and removed from the guide plate seat. The insertion and removal of DUT's in the guide plate is also performed by the mechanical handler 106. A suitable machine for use as the mechanical handler in the preferred embodiment is manufactured by Seiko-Epson under the model name HM 3500, which is a form of pick-and-place handler. The handler 106 is controlled by the tester to place a DUT in the guide plate seat to start the testing procedure. The upper and lower parts of the mounting arrangement are then brought together and testing of the DUT is performed, as described further below. Then, the mounting arrangement is opened again and the DUT is removed from the guide plate seat by the mechanical handler. According to the results of the tests on the DUT, the device is then controlled by the tester to place the DUT in, for example, a "pass" batch or a "fail" batch. The procedure is then repeated for the next DUT.

The upper part 240 of the mounting arrangement 200 has a circuit board 206 with a lower surface in a facing relationship with the upper surface of the guide plate 204. Affixed to the lower surface of circuit board 206 is a second surface mount matrix 208. The surface mount matrix 208 is positioned so that, when the upper and lower parts of the mounting arrangement are brought together, the matrix 208 is aligned with the electrical contacts 222 of the DUT in the guide plate seat. The contacts of the second surface mount matrix are coupled by way of tracks on the circuit board 206 to respective contact lands 214 also positioned on the lower surface of the circuit board 206. The contact lands 214 are aligned with the ends of respective ones of the contact elements 210 which extend from the upper surface of the guide plate.

According to the above described structure of the mounting arrangement 200, when a DUT 220 is positioned in the seat 224 of the guide plate 204, and the upper and lower parts (240, 230) are brought together in the test head, electrical connections are made between the electrical contacts 222 of the DUT and the interface board, whilst allowing light from the integrating sphere (FIG. 1) to shine on the light sensing array 221 of the DUT through apertures 203 and 225. The electrical connections are formed from the DUT electrical contacts 222 through the second surface mount matrix 208, the circuit board 206, contact lands 214, contact elements 210, the first surface mount matrix 212, and contact lands 216. Thus, signals can be communicated to and from the DUT during testing, by way of the interface board 202 in the test head, from the tester 108 and test signal processor 112 (FIG. 1).

Figure 3:
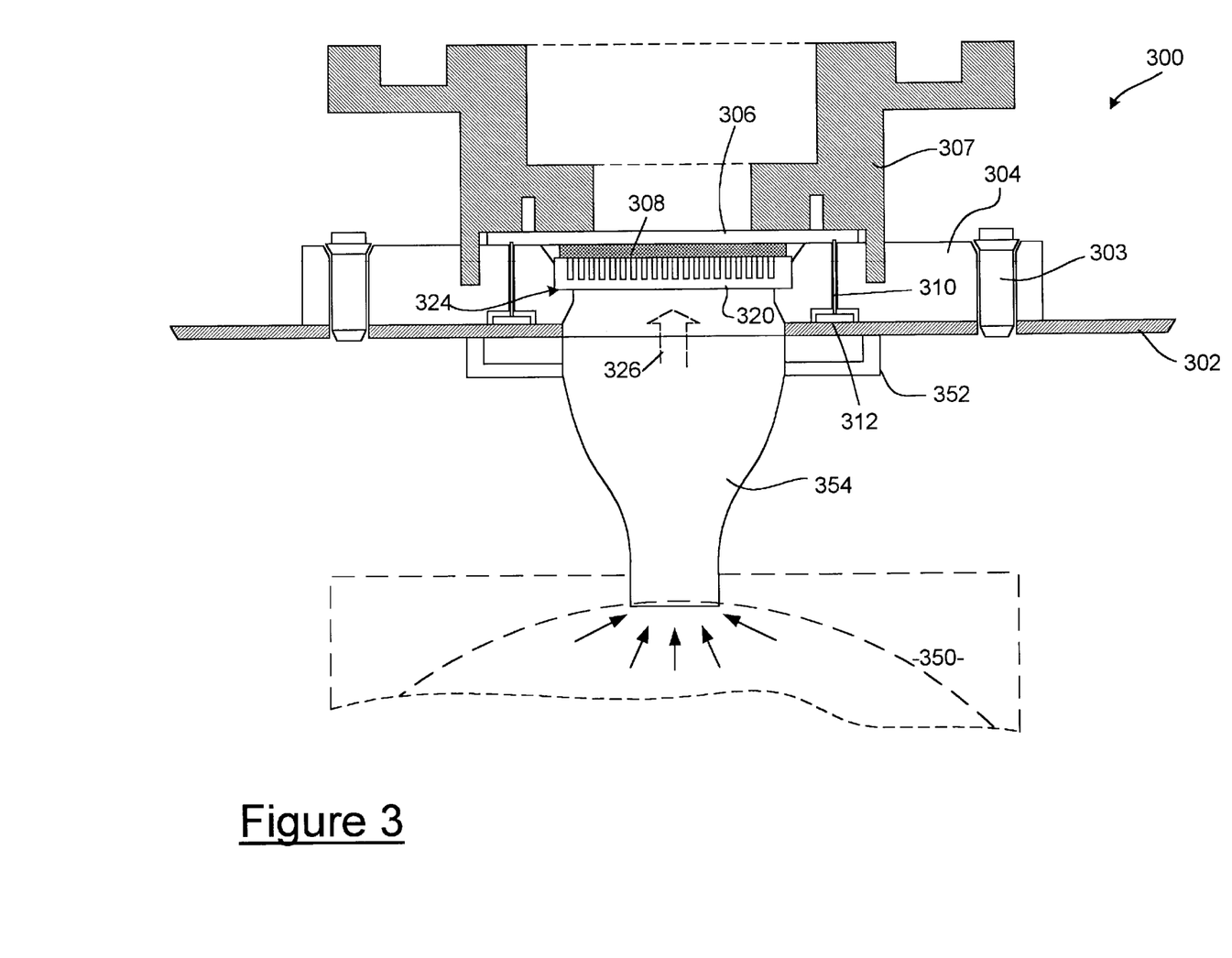
FIG. 3 is cut-away view of a test-head mounting structure.

FIG. 3 is a cut-away view of a practical implementation of the mounting arrangement 200 shown in FIG. 2. The test head mount 300 shown therein operates on the same principle as the mounting arrangement shown in FIG. 2 and described above, and a similar number system is employed to refer to equivalent components. For example, in FIG. 2 the interface board is referred to by the reference numeral 202, and in FIG. 3 the equivalent interface board component is given the reference numeral 302.

On the interface board 302 is mounted the guide plate 304, which is held in correct position by means of alignment pins 303. A DUT 320 is shown seated in the guide plate seat 324. The first surface mount matrix 312 lies between the interface board and the guide plate, in electrical contact with contact lands on the interface board (not shown in FIG. 3). The contact elements 310 extend through the guide plate from the first surface mount matrix to the upper surface of the guide plate whereby to make electrical contact with contact lands (not shown) on the circuit board 306. The circuit board 306 is attached to an upper mount assembly 307 which is moveable toward and away from the guide plate. The upper mount assembly 307 is shown in its position closest the guide plate 304 wherein electrical contact is maintained between the contact lands on circuit board 306 and the ends of contact elements 310. In this position, also, electrical contact is maintained between the second surface mount matrix 308, attached to circuit board 306, and the electrical contacts of the DUT seated in the guide plate.

At the underside of the interface board 302 (i.e. the opposite side of the interface board to that which the guide plate is mounted), an adapter mount 352 is attached over the light transmission aperture formed therein. The adapter mount 352 is used to attach a tapered coherent fused fiber optic bundle 354 to direct incident light from the integrating sphere 350 to the DUT in the direction indicated by arrow 326. The integrating sphere 350 illustrated in dashed lines in FIG. 3 corresponds to the component 110 shown in FIG. 1 and described above. As described above, light is supplied to the integrating sphere through a fiber optic cable. The tapered coherent fused fiber optic bundle 354 is provided between the integrating sphere and the DUT in order to ensure a flat field of light on the DUT light sensing array, which is not otherwise possible where there is a gap between the integrating sphere output aperture and the surface of the DUT. The end of the fused fiber optic bundle 354 which is coupled to the integrating sphere 350 accepts light incident thereon from a wide angular range, thus capturing the flat field light from the integrating sphere output. The light is conveyed through the outwardly tapering fused fiber optic bundle to the other end thereof which is adjacent the DUT light sensing array. The light output from this end of the fused fiber optic bundle is highly directional perpendicular to the end surface, in the direction indicated by arrow 322. A suitable tapered coherent fused fiber optic bundle for use in embodiments of the present invention is available from Collimated Holes, Inc. of Campbell, Calif.

Figure 4:
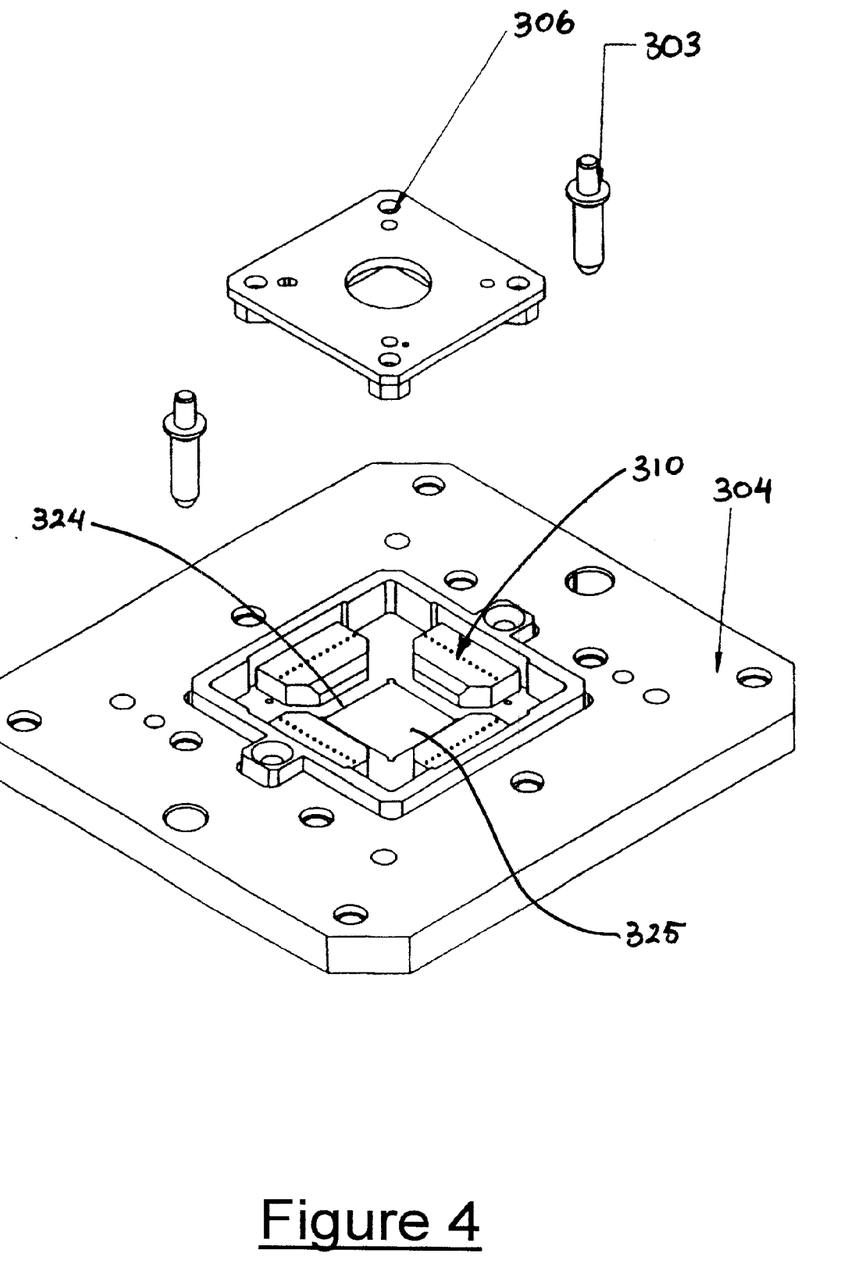
FIG. 4 is an isometric view of a portion of the test-head mounting structure of FIG. 3.

Portions of the test head mount 300 are also shown in isometric exploded view in FIG. 4, wherein common reference numerals with FIG. 3 are utilized. In particular, an upper view of the guide plate 304 is provided showing the seat 324 for receiving the DUT (not illustrated in this Figure). The guide plate seat 324 surrounds the light transmission aperture 325 formed though the center of the guide plate. Positioned around the guide plate seat are shown the projecting ends of the contact pins 310. The guide plate alignment pins 303 are also shown in this Figure, together with the circuit board 306 for making connection between the DUT electrical contacts and the contact pins 310.

The above described structure of the preferred embodiment of the present invention enables image sensing integrated circuits such as CMOS image sensors to be tested following circuit fabrication in a manner of efficiency which is heretofore unknown in the prior art. One of the ways in which the efficiency of testing is increased, and thus cost of testing decreased, is through increased speed of processing the output signals from the DUT which are used to determine whether or not the DUT passes or fails testing. The processing speed is increased firstly through the use of a high speed data link from the test head of the testing apparatus to the test signal processor. As described above, the preferred form of the test apparatus utilizes a low voltage differential signal data transfer link from the test head to an image data interface card in the test signal processor computer. Prior art testing systems have been known to have a data bottleneck in transferring data from the DUT to the tester where the output signal analysis was performed. For example in prior art testers it has been known to take up to about one second simply to move the test result data from the test head to the tester for analysis. With mega-pixel class image sensors and perhaps 20 or so tests being performed on each DUT, such data transfer performance can significantly limit the speed at which testing of a large batch of image sensors can be completed. The high speed data path of the preferred embodiment allows they data transfer delay to be reduced to a fraction of that required by the prior art testers.

The preferred embodiment also employs a dedicated test signal processor having one or more high speed DSP boards capable of several gigaFlops processing performance, in the interests of reducing testing times. Known prior art testers have employed digital signal processing circuitry included in the tester (108), which can prove inadequate for high speed analysis of the tests which are desirable for modern image sensors such as defect analysis, uniformity and bad pixels tests. Accordingly, the present invention provides the above described dedicated test signal processing circuitry, which receives the test signals from the DUT via the fast data link in order to analyze the DUT test performance with maximum speed and efficiency. Since the testing is still performed primarily under the guidance of the tester, the test signal processor and tester are coupled to communicate with one another, as above described, by way of an ethernet network connection. Prior art testers using in-built digital signal processing can take more than one minute to complete testing for each device. In contrast, the testing apparatus of the preferred embodiment can test each device in about 7 to 10 seconds, which represents a significant cost savings where testing costs are assessed at 5 cents per second.

The optical system of the preferred embodiment is also superior as compared to the prior art, which further contributes to the efficiency and speed of testing which can be achieved by the testing apparatus of the present invention. Previously known image sensor testing apparatus have utilized an optical system including filters which are mounted on wheels or the like which are mechanically rotatable for the purpose of adjusting the light characteristics at the output of the optical system. Typically such a filtering arrangement might have a plurality of filter and lens wheels mounted between a light source and an integrating sphere which provides the light output. However, several difficulties are associated with an optical system of that type, including sensitivity of the mechanical filtering system to alignment and calibration, and dust formation on the filter/lens wheel surfaces. Furthermore, the mechanical rotation of the filter wheels can require several hundred milliseconds to change filter settings. Whilst that time lag may be unimportant in the prior art testing systems where longer time is in any event required for data transfer and the like, in the high speed testing system of the present invention that loss of time is significant. The preferred embodiment described herein, therefore, overcomes the difficulties identified in the prior art by using an electronically controlled light box which is coupled between the light source and integrating sphere by way of large optical fibers. The light box includes an electronically controlled neutral density filter in the form of a liquid crystal attenuator and an electronic shutter. This optical system is not subject to the limitations of the mechanical arrangement of the prior art, and can be changed from one setting to the next in a matter of a coupled of milliseconds through an almost continuously adjustable range of about 15 to 180 lux. The filter box can also include an electronically controlled color sequence filter, and if desired a passive color shift filter to compensate for any transmission losses which may occur in the optic fibers so as to obtain the desired color temperature output at the integrating sphere.

The foregoing detailed description of the present invention has been presented by way of example only, and it is contemplated that changes and modifications may be made by one of ordinary skill in the art, to the materials and arrangements of elements of the present invention without departing from the scope of the invention. For example, various specific items of equipment are described as suitable for use in the preferred embodiment, but of course other apparatus may equally be used and may be functionally equivalent for the purposes of carrying out the present invention.

We claim:

1. A testing apparatus for testing image sensing integrated circuits, said testing apparatus comprising:
   a test head adapted to receive an integrated circuit under test, the test head having electrical contacts for making electrical connections to the integrated circuit;
   a light source;
   a light source output arranged to shine regulated test light on a light sensing portion of the integrated circuit;
   a light box, said light box incorporating an electronic filter disposed in a path of light from said light source to be modified before reaching said light source output;
   controlling circuitry coupled to communicate with the integrated circuit by way of said electrical connections to control functions of the integrated circuit during testing; and
   dedicated processing circuitry coupled through a fast data channel to the integrated circuit by way of said electrical connections to receive output signals from the integrated circuit during testing, the dedicated processing circuitry being adapted to analyze the output signals for the purpose of determining whether the integrated circuit under test meets predetermined test criteria.

2. A testing apparatus as claimed in claim 1 wherein the controlling circuitry is coupled to communicate with the dedicated processing circuitry, and wherein the controlling circuitry communicates testing parameters and pass/fail test limits to the dedicated processing circuitry and the dedicated processing circuitry communicates to the controlling circuitry indications of whether the integrated circuit under test passes or fails testing according to the output signal analysis.

3. A testing apparatus as claimed in claim 2, said testing apparatus further comprising
   mechanical apparatus for inserting and positioning the integrated circuit under test to make connection to said electrical contacts and for removing the integrated circuit following completion of testing, the removing operation of the mechanical apparatus being controlled by said controlling circuitry according to said indications of whether the integrated circuit under test passes or fails testing.

4. A testing apparatus as claimed in claim 2 wherein the fast data channel coupling the integrated circuit under test to the dedicated processing circuitry comprises a low-voltage differential signal connection.

5. A testing apparatus as claimed in claim 4 wherein the dedicated processing circuitry comprises a computer equipped with one or more digital signal processor cards.

6. A testing apparatus as claimed in claim 1, said testing apparatus further comprising:
   a first optic fiber to carry light from said light source to the light box; and
   a second optic fiber to carry light from said light box to said test head.

7. A testing apparatus as claimed in claim 1 wherein the light box incorporates an electronically controlled shutter.

8. A testing apparatus as claimed in claim 7 wherein the electronic filter includes a neutral density tunable liquid crystal attenuator.

9. A testing apparatus as claimed in claim 1 wherein the light box incorporates a fixed color shift filter.

10. A testing apparatus as claimed in claim 1 wherein the electronic filter includes an electronic color sequence filter.

11. A testing apparatus as claimed in claim 7 wherein the electronic filter and shutter are controlled by the tester.

12. A testing apparatus as claimed in claim 1 wherein the light source output comprises an integrating sphere device for providing a flat field light output.

13. A testing apparatus as claimed in claim 12 wherein the light source output further comprises a tapered coherent fused fiber optic bundle coupled to the output of the integrating sphere device to convey said flat field light output to shine on said light sensing portion of the integrated circuit.

14. A testing apparatus as claimed in claim 3 wherein the test head includes:
   a base portion having a seat for positioning the integrated circuit under test, said light source output being mounted to the base portion and an aperture being provided to allow light from the light source output to shine on the integrated circuit light sensing portion when positioned in the seat, the base portion further having electrical contact elements for coupling signals to the controlling circuitry and the dedicated processing circuitry; and
   a connecting portion which is moveable between open and closed positions relative to the base portion, the connecting portion having electrical input contacts which provide connections between the electrical contact elements of the base portion and contacts of the integrated circuit under test when positioned in said seat and with the connecting portion in said closed position.

15. A method for testing image sensing integrated circuits, said method comprising:
   positioning an integrated circuit in a test head in relation to a light source output; making electrical connections to said integrated circuit;
   providing light from a regulated light source to a light box having electronic filter and shutter control and from the light box to the light source output to shine regulated light on a light sensing portion of the integrated circuit;
   providing first control signals from a tester to the integrated circuit by way of said test head to control the integrated circuit during testing;
   providing second control signals to the light box to control the electronic filter and shutter during testing;
   transferring output signals from the integrated circuit during testing to processing circuitry by way of a high speed data channel coupled between the test head and the processing circuitry; and analyzing the output signals in the processing circuitry to determine whether the integrated circuit passes or fails testing.

16. A method as claimed in claim 18 and wherein the controlling circuitry communicates testing parameters and pass/fail test limits to the processing circuitry and the processing circuitry communicates to the controlling circuitry indications of whether the integrated circuit under test passes or fails testing according to the output signal analysis.

17. A method as claimed in claim 18 wherein the test head includes mechanical apparatus for inserting and positioning the integrated circuit under test to make connection to said electrical contacts and for removing the integrated circuit following completion of testing, the method further including controlling the removing operation of the mechanical apparatus by said controlling circuitry according to said indications of whether the integrated circuit under test passes or fails testing.

18. A method as claimed in claim 15 wherein the high speed data channel coupling the integrated circuit under test to the dedicated processing circuitry comprises a low-voltage differential signal connection.

19. A testing apparatus for testing image sensing integrated circuits, said testing apparatus comprising:
 a regulated light source;
 a light box coupled to said regulated light source, said light box comprising an electronically controlled filter;
 a test head adapted to receive an integrated circuit under test, the test head having electrical contacts for making electrical connections to the integrated circuit and a light source output arranged to shine regulated test light on a light sensing portion of the integrated; and
 controlling circuitry, said controlling circuitry coupled to communicate with the integrated circuit by way of said electrical connections to control functions of the integrated circuit during testing, said controlling circuitry coupled to said light box to control said electronically controlled filter.

* * * * *